US010493178B2

(12) United States Patent
Marchant et al.

(10) Patent No.: US 10,493,178 B2
(45) Date of Patent: *Dec. 3, 2019

(54) HYDROGEL COMPOSITIONS

(71) Applicant: Lubrizol Advanced Materials, Inc., Cleveland, OH (US)

(72) Inventors: Nancy S. Marchant, Medina, OH (US); James R. Baxter, Macedonia, OH (US); Paul M. Basone, Akron, OH (US)

(73) Assignee: Lubrizol Advanced Materials, Inc., Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/324,888

(22) PCT Filed: Jul. 9, 2015

(86) PCT No.: PCT/US2015/039649
§ 371 (c)(1),
(2) Date: Jan. 9, 2017

(87) PCT Pub. No.: WO2016/007692
PCT Pub. Date: Jan. 14, 2016

(65) Prior Publication Data
US 2017/0202999 A1    Jul. 20, 2017

Related U.S. Application Data

(60) Provisional application No. 62/022,245, filed on Jul. 9, 2014.

(51) Int. Cl.
*A61L 26/00* (2006.01)
*A61K 9/00* (2006.01)
(Continued)

(52) U.S. Cl.
CPC .......... *A61L 26/0052* (2013.01); *A61K 8/042* (2013.01); *A61K 8/8141* (2013.01);
(Continued)

(58) Field of Classification Search
None
See application file for complete search history.

(56) References Cited

U.S. PATENT DOCUMENTS 2,340,110 A    1/1944   D'Alelio
2,340,111 A    1/1944   D'Alelio
(Continued)

FOREIGN PATENT DOCUMENTS

EP    1829563    *    9/2007
EP    1829563 A1     9/2007
(Continued)

OTHER PUBLICATIONS

Yang et al., Macromolecules 1996, 29, 7047-7054 (Year: 1996).*
(Continued)

*Primary Examiner* — Karl J Puttlitz
(74) *Attorney, Agent, or Firm* — Thoburn Dunlap (57) ABSTRACT

A hydrogel composition from a cross-linked polymer derived from one or more olefinically unsaturated polymerizable carboxylic monomers and a thermoplastic polyurethane composition is disclosed. The hydrogel exhibits high yield stress at low shear. The hydrogel composition provides useful materials for personal care, health care, medical and pharmaceutical applications, among others.

26 Claims, 1 Drawing Sheet

(51) Int. Cl.

| | |
|---|---|
| A61K 9/06 | (2006.01) |
| A61K 47/32 | (2006.01) |
| A61L 15/22 | (2006.01) |
| A61L 15/60 | (2006.01) |
| A61K 8/04 | (2006.01) |
| A61K 8/81 | (2006.01) |
| A61K 8/87 | (2006.01) |
| A61K 31/05 | (2006.01) |
| A61K 31/125 | (2006.01) |
| A61K 31/167 | (2006.01) |
| A61K 47/34 | (2017.01) |
| A61Q 19/00 | (2006.01) |
| C08L 33/02 | (2006.01) |
| C08L 75/04 | (2006.01) |

(52) U.S. Cl.
CPC .............. *A61K 8/87* (2013.01); *A61K 9/0014* (2013.01); *A61K 9/06* (2013.01); *A61K 31/05* (2013.01); *A61K 31/125* (2013.01); *A61K 31/167* (2013.01); *A61K 47/32* (2013.01); *A61K 47/34* (2013.01); *A61L 15/225* (2013.01); *A61L 15/60* (2013.01); *A61L 26/008* (2013.01); *A61Q 19/00* (2013.01); *C08L 33/02* (2013.01); *C08L 75/04* (2013.01); *A61K 2800/48* (2013.01)

(56) References Cited

U.S. PATENT DOCUMENTS

| | | |
|---|---|---|
| 2,533,635 A | 12/1950 | Seymour |
| 2,798,053 A | 7/1957 | Brown |
| 3,915,921 A | 10/1975 | Schlatzer, Jr. |
| 3,940,351 A | 2/1976 | Schlatzer, Jr. |
| 4,062,817 A | 12/1977 | Westerman |
| 4,203,877 A | 5/1980 | Baker |
| 4,267,103 A | 5/1981 | Cohen |
| 5,034,486 A | 7/1991 | Tzai et al. |
| 5,034,487 A | 7/1991 | Tazi et al. |
| 5,034,488 A | 7/1991 | Tazi et al. |
| 5,288,814 A | 2/1994 | Long, II et al. |
| 5,349,030 A | 9/1994 | Long, II et al. |
| 5,563,233 A | 10/1996 | Reich et al. |
| 2002/0015726 A1 | 2/2002 | Scamilla Aledo et al. |
| 2008/0311071 A1 | 12/2008 | Hardy et al. |

FOREIGN PATENT DOCUMENTS

| | | |
|---|---|---|
| WO | 2013/180937 A1 | 12/2013 |
| WO | 2013180937 | * 12/2013 |

OTHER PUBLICATIONS

Yang et al., Macromolecules 1996, 29, 7055-7063 (Year: 1996).*
Baek et al., Colloids and Surfaces a: Physicochem. Eng. Aspects 220 (2003) 191-198 (Year: 2003).*

* cited by examiner

HYDROGEL COMPOSITIONS

CROSS REFERENCE TO RELATED APPLICATION

This application claims priority from PCT Application Serial No. PCT/US2015/0039649 filed on Jul. 9, 2015, which claims the benefit of U.S. Provisional Application No. 62/022,245 filed on Jul. 9, 2014, both of which are incorporated in their entirety by reference herein.

The invention relates to a hydrogel composition formed from a cross-linked poly(acrylic) acid and a thermoplastic polyurethane. The hydrogels of the invention can be employed as a gelling and binding agent, thickeners, stabilizers, emulsifiers, spreading and deposition aids and carriers for enhancing the rheology, efficacy, deposition, psychosensory, aesthetic and delivery of chemically and physiologically active ingredients in personal care, health care, and pharmaceutical applications.

BACKGROUND OF THE INVENTION

Hydrogels are polymers that swell in water. The term, "swelling" refers to the uptake of a liquid by a gel with an increase in volume. Only those liquids that solvate a gel can cause swelling. The swelling of ionic hydrogel gels is influenced by pH and the presence of electrolytes. Microgels have a large molecular weight that generally cannot be measured by conventional methods because they are too large, and are composed of a polymer backbone and crosslinks. The crosslinks can be used to extend the molecular weight of a polymer if the ratio of crosslinker to non-crosslinker is low, and polymerization is confined below the gel point. Nevertheless, if the ratio of crosslinking monomer to non-crosslinking monomer is high enough, a gel is formed that while still being able to swell in a solvent, does not truly dissolve.

The viscosity behavior of crosslinked polyelectrolyte microgels has been understood in terms of a model based on close packed spheres. At low concentrations, no yield stress (where yield stress is defined as the applied stress which must be exceeded to make a structural fluid flow) and little viscosity is observed because the swollen microgels are not tightly packed. Above some minimum packing concentration the particles are viewed as being closely packed deformable particles and the viscosity builds tremendously. Yield behavior and viscosity only begins when the concentration is such that the particles become closely packed.

The solution viscosity behavior of thermoplastic polyurethane is that of a linear polymer in a random configuration. The viscosity is dependent on both the molecular weight of the polymer and the solvency of the dissolution media. A linear randomly coiled polymer will have an intrinsic viscosity at low concentration that relates to the volume of the polymer and to the molecular weight. At higher concentrations, entanglement of the random coils will increase the apparent viscosity of the solution. Solutions of linear polymers in a random configuration usually do not show yield behavior and are not able to suspend particles.

In characterizing these materials used as thickeners, emulsifiers and suspending aids, the response of these materials to stress and simple flow fields may be used to determine their material functions, such as viscosity and response to stress.

Mathematical models have been developed to describe these properties. Rheological measurements on gels or thickened and suspended materials define the structure and properties of the material and can be used to identify changes and characteristics of an improved material over that being currently used. To those skilled in the art, interpretation of the response of a polymeric dispersion or gel to stress and strain is highly indicative of the material.

There is currently a need for polymeric compositions having high yield point, yield stress properties, as well as high response to shear as well as a need for improved methods of making these polymer compositions. There is also a need for improved polymeric compositions for use as thickeners, emulsifiers, suspending aids, and pharmaceutical controlled release excipients.

SUMMARY OF THE INVENTION

The disclosed technology provides a hydrogel composition that displays a strong viscosity profile at low shear with pleasant sensory characteristics. The gel as disclosed herein provides the thickening associated with a poly(acrylic) acid polymer in combination with good mechanical properties attributed to a thermoplastic polyurethane (TPU).

The invention provides a hydrogel including a crosslinked polymer derived from one or more olefinically unsaturated polymerizable carboxylic monomers, an optional comonomer, and a thermoplastic polyurethane (TPU) which includes the reaction product of i) a polyisocyanate and a polyol component including at least one polyethylene glycol polyol in which the composition exhibits high yield stress at low shear.

The invention further provides the hydrogel described herein in which the cross-linked polymer is a carbomer copolymer, a carbomer homopolymer, a carbomer interpolymer, or a polycarbophil.

The invention further provides the hydrogel described herein in which the poly(acrylic) acid polymer is cross-linked with an allyl ether cross-linking agent or a divinyl glycol.

The invention further provides the hydrogel described herein in which the allyl ether cross-linking agent includes one or more of an allyl pentaerythritol, allyl sucrose, trimethylolpropane diallyl ether (TMPDE)

The invention further provides the hydrogel described herein in which the thermoplastic polyurethane includes the reaction product of (i) at least one aliphatic or aromatic diisocyanate; (ii) a polyol component comprising at one polyethylene gylocol polyol having a number average molecular weight of at least 1450 and (ii) optionally, a chain extender component.

The invention further provides the hydrogel described herein in which the aliphatic diisocyanate comprises H12MDI.

The invention further provides the hydrogel described herein in which the aromatic diisocyanate comprises MDI, TDI or XDI.

The invention further provides the hydrogel described herein in which the chain extender component comprises an aliphatic diol.

The invention further provides the hydrogel described herein in which the polyol component comprises a blend of polyethylene glycol having number average molecular weights (Mn) of at least 300 and at least 1450.

The invention further provides the hydrogel described herein in which the polyol component comprises a blend of polyethylene glycol having number average molecular weights (Mn) of at least 1450 and at least 8000.

The invention further provides the hydrogel described herein in which the cross-linked polymer is partially neutralized.

The invention further provides the hydrogel described herein further including a comonomer including one or more of at least one acrylic acid ester of the formula:

wherein $R^3$ is hydrogen, methyl or ethyl and $R^4$ is an alkyl group containing 1 to 30 carbon atoms, in an amount of less than 30 weight percent based upon the weight of the carboxylic acid or anhydride plus the acrylic acid ester.

The invention further provides the hydrogel described herein in which the ratio of the cross-linked polymer to the thermoplastic polyurethane is from about 1:9 to about 2:1.

The invention further provides the hydrogel in which the hydrophilic thermoplastic polyurethane forms about 0.02 wt % to 1.5 wt % of the total weight of the composition.

The invention further provides the hydrogel in which the crosslinked polymer forms from about 0.01 wt % to about 1.0 wt % of the total weight of the composition.

The invention further provides the hydrogel described herein further including a pharmaceutical, a biologically active compound, an absorptive material, a personal care compound, an active ingredient, a therapeutic aid, or combinations thereof.

The invention further provides a wound covering including the hydrogel described herein.

The invention further provides a gel, a cream or a lotion including the hydrogel described herein.

The invention further provides a hydrogel including a thermoplastic polyurethane which is water soluble.

The invention further provides a hydrogel having a viscosity of from 3,000 to 200,000 mPa*s.

The invention further provides a hydrogel having a yield stress as measured by Brookfield of from 50 to 2500 Pas.

The invention further provides a chain extender component including one or more of diethylene glycol or a $C_3$-$C_{12}$ diol in an amount from 0.4 wt % to 4.0 wt %.

The invention further provides a hydrogel composition including a crosslinked polymer derived from one or more olefinically unsaturated polymerizable carboxylic monomers, an optional comonomer and a thermoplastic polyurethane (TPU) including the reaction product of an aliphatic diisocyanate and a polyol component including of at least one polyethylene glycol having a number average molecular weight (Mn) of at least 1450, in which the composition exhibits high yield stress at low shear.

The invention further provides a process of making a hydrogel composition, the process including the steps of: (I) reacting a) a crosslinked polymer derived from one or more olefinically unsaturated polymerizable carboxylic monomers; and b) a thermoplastic polyurethane which includes the reaction product of i) an aliphatic or aromatic and ii) a polyol component comprising of at least one polyethylene glycol polyol, the resulting hydrogel composition has a viscosity of from 3,000 to 200,000 mPa*s.

The invention further provides a process of making a hydrogel in which the diisocyanate comprises H12MDI, MDI, TDI, or XDI.

The invention further provides a hydrogel composition which includes a) a homopolymer of a crosslinked polymer derived from one or more olefinically unsaturated polymerizable carboxylic monomers; and b) a hydrophilic thermoplastic polyurethane, the hydrogel composition exhibiting a viscosity of from 3,000 to 200,000 mPa*s, a shear response as measured by microviscosity of from 130 mPa*s to about 2,500 mPa*s.

The invention further provides a hydrogel composition in which the composition exhibits a yield stress as measured by Brookfield of from 50 to 2500 Pas.

DETAILED DESCRIPTION OF THE INVENTION

Various preferred features and embodiments will be described below by way of non-limiting illustration.

The hydrogel described herein is prepared from a solution containing at least two polymers, namely, a partially-neutralized, cross-linked polymer and a water soluble thermoplastic polyurethane (TPU). By "gel" it is meant that the viscosity will, in one embodiment, be from 3,000 Cps to 200,000 mPa*s, and in another embodiment, from 3,000 to 150,000 mPa*s, or from 3,000 to 120,000 mPa*s, as tested by Brookfield rotating spindle method at 20 RPM.

The term poly(acrylic) acid or acrylic acid polymer is used to encompass a variety of polymers having high percentages of polymerizable monomers therein with pendant carboxylic acid groups or anhydrides of polycarboxylic acid. These are described in more detail in U.S. Pat. Nos. 2,798,053; 3,915,921; 4,267,103; 5,288,814; and 5,349,030 hereby incorporated by reference. The term polyacrylic acid is used to include various homopolymers, copolymers, and interpolymers, wherein at least 50 or 75 mole percent of the repeating units have pendant carboxylic acid groups or anhydrides of dicarboxylic acid groups. While acrylic acid is the most common primary monomer used to form polyacrylic acid the term is not limited thereto but includes generally all α-β unsaturated monomers with carboxylic pendant groups or anhydrides of dicarboxylic acids as described in U.S. Pat. No. 5,349,030.

The carboxyl containing polymers are prepared from monomers containing at least one activated >C=C< group and carboxyl group. Such polymers are homopolymers of an unsaturated, polymerizable carboxylic monomers such as acrylic acid, methacrylic acid, maleic acid, itaconic acid, maleic anhydride, and the like, and copolymers of polymerizable carboxylic monomers with acrylate esters, acrylamides, olefins, vinyl esters, vinyl ethers, or styrenics. The carboxyl containing polymers have molecular weights greater than about 500 to as high as several million, usually greater than about 10,000 to 900,000 or more.

Copolymers, for example, include copolymers of acrylic acid with small amounts of polyalkenyl polyether crosslinkers that are gel-like polymers, which, especially in the form of their salts, absorb large quantities of water or solvents with subsequent substantial increase in volume. Other useful carboxyl containing polymers are described in U.S. Pat. No. 3,940,351, directed to polymers of unsaturated carboxylic acid and at least one alkyl acrylic or methacrylic ester where the alkyl group contains 10 to 30 carbon atoms, and U.S. Pat. Nos. 5,034,486; 5,034,487; and 5,034,488; which are directed to maleic anhydride copolymers with vinyl ethers. Other types of such copolymers are described in U.S. Pat. No. 4,062,817 wherein the polymers described in U.S. Pat. No. 3,940,351 contain additionally another alkyl acrylic or methacrylic ester and the alkyl groups contain 1 to 8 carbon atoms. Carboxylic polymers and copolymers such as those of acrylic acid and methacrylic acid also may be cross-linked with polyfunctional materials as divinyl benzene, unsaturated diesters and the like, as is disclosed in U.S. Pat. Nos. 2,340,110; 2,340,111; and 2,533,635. The disclosures of all of these U.S. Patents are hereby incorporated herein by reference.

The carboxylic monomers are the olefinically-unsaturated carboxylic acids containing at least one activated carbon-to-carbon olefinic double bond, and at least one carboxyl group; that is, an acid or function readily converted to an acid containing an olefinic double bond which readily functions in polymerization because of its presence in the monomer molecule, either in the alpha-beta position with respect to a carboxyl group, —C=C—COOH; or as part of a terminal methylene grouping, $CH_2=C<$. Olefinically-unsaturated acids of this class include such materials as the acrylic acids typified by the acrylic acid itself, alpha-cyano acrylic acid, beta methylacrylic acid (crotonic acid), alpha-phenyl acrylic acid, beta-acryloxy propionic acid, cinnamic acid, p-chloro cinnamic acid, 1-carboxy-4-phenyl butadiene-1,3, itaconic acid, citraconic acid, mesaconic acid, glutaconic acid, aconitic acid, maleic acid, fumaric acid, and tricarboxy ethylene. As used herein, the term "carboxylic acid" includes the polycarboxylic acids and those acid anhydrides, such as maleic anhydride, wherein the anhydride group is formed by the elimination of one molecule of water from two carboxyl groups located on the same carboxylic acid molecule. Maleic anhydride and other acid anhydrides useful herein have the general structure wherein R and R' are selected from the group consisting of hydrogen, halogen and cyanogen (—C≡N) groups and alkyl, aryl, alkaryl, aralkyl, and cycloalkyl groups such as methyl, ethyl, propyl, octyl, decyl, phenyl, tolyl, xylyl, benzyl, cyclohexyl, and the like.

The preferred carboxylic monomers are the monoolefinic acrylic acids having the general structure:

wherein $R^2$ is a substituent selected from the class consisting of hydrogen, halogen, and the cyanogen (—C≡N) groups, monovalent alkyl radicals, monovalent aryl radicals, monovalent aralkyl radicals, monovalent alkaryl radicals and monovalent cycloaliphatic radicals. Of this class, acrylic and methacrylic acid are most preferred. Other useful carboxylic monomers are maleic acid and its anhydride.

The polymers include both homopolymers of carboxylic acids or anhydrides thereof, or the defined carboxylic acids copolymerized with one or more other vinylidene monomers containing at least one terminal >C=$CH_2$ group. The other vinylidene monomers are present in an amount of less than 30 weight percent based upon the weight of the carboxylic acid or anhydride plus the vinylidene monomer(s). Such monomers include, for example, acrylate ester monomers including those acrylic acid ester monomers such as derivatives of an acrylic acid represented by the formula wherein $R^4$ is an alkyl group having from 1 to 30 carbon atoms, preferably 1 to 20 carbon atoms and $R^3$ is hydrogen, methyl or ethyl, present in the copolymer in amount, for example, from about 1 to 40 weight percent or more. Representative acrylates include methyl acrylate, ethyl acrylate, propyl acrylate, isopropyl acrylate, butyl acrylate, isobutyl acrylate, methyl methacrylate, methyl ethacrylate, ethyl methacrylate, octyl acrylate, heptyl acrylate, octyl methacrylate, isopropyl methacrylate, 2-ethylhexyl methacrylate, nonyl acrylate, hexyl acrylate, n-hexyl methacrylate, and the like. Higher alkyl acrylic esters are decyl acrylate, isodecyl methacrylate, lauryl acrylate, stearyl acrylate, behenyl acrylate and melissyl acrylate. Mixtures of two or three or more long chain acrylic esters may be successfully polymerized with one of the carboxylic monomers. Other comonomers include olefins, including alpha olefins, vinyl ethers, vinyl esters, and mixtures thereof.

The polymers also may be cross-linked with any polyene, e.g. decadiene or trivinyl cyclohexane; acrylamides, such as methylene bis acrylamide; polyfunctional acrylates, such as trimethylol propane triacrylate; or polyfunctional vinylidene monomer containing at least 2 terminal $CH_2=C<$ groups, including for example, butadiene, isoprene, divinyl benzene, divinyl naphthlene, allyl acrylates and the like. Particularly useful cross-linking monomers for use in preparing the copolymers are polyalkenyl polyethers having more than one alkenyl ether grouping per molecule. The most useful possess alkenyl groups in which an olefinic double bond is present attached to a terminal methylene grouping, $CH_2=C<$. They are made by the etherification of a polyhydric alcohol containing at least 2 carbon atoms and at least 2 hydroxyl groups. Compounds of this class may be produced by reacting an alkenyl halide, such as allyl chloride or allyl bromide, with a strongly alkaline aqueous solution of one or more polyhydric alcohols. The product may be a complex mixture of polyethers with varying numbers of ether groups. Analysis reveals the average number of ether groupings on each molecule. Efficiency of the polyether cross-linking agent increases with the number of potentially polymerizable groups on the molecule. It is preferred to utilize polyethers containing an average of two or more alkenyl ether groupings per molecule. Other cross-linking monomers include for example, diallyl esters, dimethallyl ethers, allyl or methallyl acrylates and acrylamides, tetraallyl tin, tetravinyl silane, polyalkenyl methanes, diacrylates, and dimethacrylates, divinyl compounds such as divinyl benzene, divinyl glycol, polyallyl phosphate, diallyloxy compounds and phosphite esters and the like. Typical agents are allyl pentaerythritol, allyl sucrose, trimethylolpropane triacrylate, 1,6-hexanediol diacrylate, trimethylolpropane diallyl ether, pentaerythritol triacrylate, tetramethylene dimethacrylate, ethylene diacrylate, ethylene dimethacrylate, triethylene glycol dimethacrylate, and the like. Allyl pentaerythritol, trimethylolpropane diallylether and allyl sucrose provide excellent polymers. When the cross-linking agent is present, the polymeric mixtures usually contain up to about 5% or less by weight of cross-linking monomer based on the total of carboxylic acid monomer, plus other monomers, if present, and more preferably about 0.01 to 3.0 weight percent.

Other vinylidene monomers may also be used, including the acrylic nitriles. The useful $\alpha,\beta$-olefinically unsaturated nitriles are preferably the monoolefinically unsaturated nitriles having from 3 to 10 carbon atoms such as acrylonitrile, methacrylonitrile, and the like. Most preferred are acrylonitrile and methacrylonitrile. The amounts used are, for example, for some polymers are from about 1 to 30 weight percent of the total monomers copolymerized. Acrylic amides containing from 3 to 35 carbon atoms including monoolefinically unsaturated amides also may be used. Representative amides include acrylamide, methacrylamide, N-t-butyl acrylamide, N-cyclohexyl acrylamide, higher alkyl amides, where the alkyl group on the nitrogen contains from 8 to 32 carbon atoms, acrylic amides including N-alkylol amides of alpha, beta-olefinically unsaturated carboxylic acids including those having from 4 to 10 carbon atoms such as N-methylol acrylamide, N-propanol acrylamide, N-methylol methacrylamide, N-methylol maleimide, N-methylol maleamic acid esters, N-methylol-p-vinyl benzamide, and the like. Still further useful materials are alpha-olefins containing from 2 to 18 carbon atoms, more preferably from 2 to 8 carbon atoms; dienes containing from 4 to 10 carbon atoms; vinyl esters and allyl esters such as vinyl acetate; vinyl aromatics such as styrene, methyl styrene and chlorostyrene; vinyl and allyl ethers and ketones such as vinyl methyl ether and methyl vinyl ketone; chloroacrylates; cyanoalkyl acrylates such as $\alpha$-cyanomethyl acrylate, and the $\alpha$-, $\beta$-, and $\gamma$-cyanopropyl acrylates; alkoxyacrylates such as methoxy ethyl acrylate; haloacrylates as chloroethyl acrylate; vinyl halides and vinyl chloride, vinylidene chloride and the like; divinyls, diacrylates and other polyfunctional monomers such as divinyl ether, diethylene glycol diacrylate, ethylene glycol dimethacrylate, ethylene-bisacrylamide, allylpentaerythritol, and the like; and bis($\beta$-haloalkyl) alkenyl phosphonates such as bis($\beta$-chloroethyl) vinyl phosphonate and the like as are known to those skilled in the art. Copolymers wherein the carboxy containing monomer is a minor constituent, and the other vinylidene monomers present as major components are readily prepared in accordance with the process of this invention.

The steric stabilizer functions to provide a steric barrier which repulses approaching particles. A requirement for the steric stabilizer is that a segment of the dispersant (i.e., a hydrophobe) be very soluble in the solvent (the continuous phase in a nonaqueous dispersion polymerization process) and that another segment (i.e., a hydrophile) be at least strongly adhered to the growing polymer particle. Thus, the steric stabilizers of the present invention have a hydrophilic group and a hydrophobic group. The steric stabilizers are block copolymers comprising a soluble block and an anchor block having a molecular weight (i.e., chain length) usually well above 1000, but a hydrophobe length of more than 50 Angstroms, as calculated by the Law of Cosines. These dimensions are determined on the extended configuration using literature values for bond lengths and angles. Thus the steric stabilizers of the present invention are distinguishable from the prior art steric surfactants which may be block copolymers, but have hydrophobe lengths of less than 50 Angstroms. The steric stabilizer of the present invention has either a linear block or a comb configuration, and has a hydrophobe of sufficient length to provide a sufficient steric barrier.

When the steric stabilizer is a linear block copolymeric steric stabilizer, it is defined by the following formula:

where A is a hydrophilic moiety, having a solubility in water at 25° C. of 1% or greater, a molecular weight of from about 200 to about 50,000, and selected to be covalently bonded to the B blocks;

B is a hydrophobic moiety, having a molecular weight of from about 300 to about 60,000, a solubility of less than 1% in water at 25° C., capable of being covalently bonded to the A blocks;

and D are terminating groups which can be A or B; can be the same or different groups, and will depend upon the manufacturing process since they are present to control the polymer length, to add other functionality, or as a result of the manufacturing process;

w is 0 or 1;

x is an integer of 1 or more, y is 0 or 1, and z is 0 or 1.

Examples of hydrophilic groups are polyethylene oxide, poly(1,3-dioxolane), copolymers of polyethylene oxide or poly(1,3-dioxolane), poly(2-methyl-2-oxazoline polyglycidyl trimethyl ammonium chloride, polymethylene oxide, and the like, with polyethylene oxide being preferred. Examples of hydrophobic groups are polyesters, such as those derived from 2-hydroxybutyric acid, 3-hydroxybutyric acid, 4-hydroxybutyric acid, 2-hydroxycaproic acid, 10-hydroxydecanoic acid, 12-hydroxydodecanoic acid, 16-hydroxyhexadecanoic acid, 2-hydroxyisobutyric acid, 2-(4-hydroxyphenoxy) propionic acid, 4-hydroxyphenylpyruvic acid, 12-hydroxystearic acid, 2-hydroxyvaleric acid, polylactones, such as caprolactone, butyrolactone, polylactams, such as those derived from caprolactam, polyurethanes, polyisobutylene, where the hydrophobe should provide a steric barrier of greater than 50 Angstroms, preferably greater than 75 Angstroms, with greater than 100 Angstroms being also preferred, and the like, with polyhydroxy fatty acids, such as poly(12-hydroxystearic acid) being preferred. The steric barrier is the length of the hydrophobe in its fully-extended condition. Such steric stabilizers are commercially available under the brand name Hypermer® from Croda.

Steric stabilizer molecules comprise both hydrophilic and hydrophobic units. Hydrophobic polymer units or hydrophobic blocks may be prepared by a number of well-known methods. These methods include condensation reactions of hydroxy acids, condensation of polyols (preferably diols) with polycarboxylic acids (preferably diacids). Other useful methods include polymerization of lactones and lactams, and reactions of polyols with polyisocyanates. Hydrophobic blocks or polymer units can be reacted with hydrophilic units by such reactions as are known to those skilled in the art. These reactions include condensation reactions and coupling reactions, for example. Subsequent to the steric stabilizer preparation, the stabilizers may be further reacted with modifying agents to enhance their utility. U.S. Pat. No. 4,203,877 to Alan S. Baker teaches making such steric stabilizers, and the entire disclosure thereof is incorporated herein by reference.

When the steric stabilizer is a random copolymeric comb steric stabilizer, it is defined by the following formula:

where $R^5$ and $R^6$ are terminating groups and may be the same or different and will be different from Z and Q, Z is a hydrophobic moiety having a solubility of less than 1% in water at 25° C., Q is a hydrophilic moiety, having a solubility of more than 1% in water at 25° C., m and n are integers of 1 or more, and are selected such that the molecular weight of the polymer is from about 100 to about 250,000.

Examples of the hydrophobic monomer unit or moiety are dimethyl siloxane, diphenyl siloxane, methylphenyl siloxane, alkyl acrylate, alkyl methacrylate, and the like, with dimethyl siloxane being preferred.

Examples of the hydrophilic monomer unit or moiety are methyl-3-polyethoxypropyl siloxane-Ω-phosphate or sulfate, and the alkali metal or ammonium salts derived therefrom; units derived from polyethoxy (meth) acrylate containing from 1 to 40 moles of ethylene oxide; acrylic acid; acrylamide; methacrylic acid, maleic anhydride; dimethyl amino ethyl (meth)acrylate; or its salts with methyl chloride or dimethyl sulfate; dimethyl amino propyl(meth)acrylamide and its salts with methyl chloride or dimethyl sulfate, and the like, with methyl-3-polyethoxypropyl siloxane-Ω-phosphate being preferred.

Examples of terminating agents are monohalo silanes, mercaptans, haloalkanes, alkyl aromatics, alcohols, and the like, which will produce terminating groups such as trialkyl silyl, alkyl, aryl alkyl, alcoholate, and the like, with the preferred terminating groups being trimethyl silyl.

Specific types of cross-linked polyacrylic acids include Carbopol® 981NF; Carbopol® 980NF; Pemulen TR1; Pemulen TR2; and carbomer interpolymer ETD-2020-NF; Ultrez 10NF, copolymers of acrylic acid and alkyl acrylates; copolymers of acrylic acid and alkyl vinyl ethers; and copolymers of ethylene and maleic anhydride. An approved polyacrylic acid for pharmaceutical applications are carbomer homopolymers, carbomer copolymers, carbomer interpolymers or polycarbophil, as described in the carbomer and polycarbophil compendia monographs in the U.S.

The TPU compositions described herein are made using a) a polyisocyanate component. The polyisocyanate and/or polyisocyanate component includes one or more polyisocyanates. In some embodiments, the polyisocyanate component includes one or more diisocyanates.

In some embodiments, the polyisocyanate and/or polyisocyanate component includes an α, ω-alkylene diisocyanate having from 5 to 20 carbon atoms.

Suitable polyisocyanates include aromatic diisocyanates, aliphatic diisocyanates, or combinations thereof. In some embodiments, the polyisocyanate component includes one or more aromatic diisocyanates. In some embodiments, the polyisocyanate component is essentially free of, or even completely free of, aliphatic diisocyanates. In other embodiments, the polyisocyanate component includes one or more aliphatic diisocyanates. In some embodiments, the polyisocyanate component is essentially free of, or even completely free of, aromatic diisocyanates.

Examples of useful polyisocyanates include aromatic diisocyanates such as 4,4'-methylenebis(phenyl isocyanate) (MDI), m-xylene diisocyanate (XDI), phenylene-1,4-diisocyanate, naphthalene-1,5-diisocyanate, and toluene diisocyanate (TDI); as well as aliphatic diisocyanates such as isophorone diisocyanate (IPDI), 1,4-cyclohexyl diisocyanate (CHDI), decane-1,10-diisocyanate, lysine diisocyanate (LDI), 1,4-butane diisocyanate (BDI), hexane-1,6-diisocyanate (HDI), 3,3'-dimethyl-4,4'-biphenylene diisocyanate (TODI), 1,5-naphthalene diisocyanate (NDI), and dicyclohexylmethane-4,4'-diisocyanate (H12MDI). Mixtures of two or more polyisocyanates may be used. In some embodiments, the polyisocyanate is MDI and/or H12MDI. In some embodiments, the polyisocyanate includes MDI. In some embodiments, the polyisocyanate includes H12MDI.

In some embodiments, the thermoplastic polyurethane is prepared with a polyisocyanate component that includes H12MDI. In some embodiments, the thermoplastic polyurethane is prepared with a polyisocyanate component that consists essentially of H12MDI. In some embodiments, the thermoplastic polyurethane is prepared with a polyisocyanate component that consists of H12MDI.

In some embodiments, the thermoplastic polyurethane is prepared with a polyisocyanate component that includes (or consists essentially of, or even consists of) H12MDI and at least one of MDI, HDI, TDI, IPDI, LDI, BDI, PDI, CHDI, TODI, and NDI.

In some embodiments, the polyisocyanate used to prepare the TPU and/or TPU compositions described herein is at least 50%, on a weight basis, a cycloaliphatic diisocyanate. In some embodiments, the polyisocyanate includes an α, ω-alkylene diisocyanate having from 5 to 20 carbon atoms.

In some embodiments, the polyisocyanate used to prepare the TPU and/or TPU compositions described herein includes hexamethylene-1,6-diisocyanate, 1,12-dodecane diisocyanate, 2,2,4-trimethyl-hexamethylene diisocyanate, 2,4,4-trimethyl-hexamethylene diisocyanate, 2-methyl-1,5-pentamethylene diisocyanate, or combinations thereof.

The Polyol Component

The TPU compositions described herein are made using b) a polyol component. Polyols include polyether polyols.

Suitable polyols, which may also be described as hydroxyl terminated intermediates, when present, may include one or more hydroxyl terminated polyethers, polyether/polyester blocks, or mixtures thereof.

Suitable hydroxyl terminated polyether intermediates include polyether polyols derived from a diol or polyol having a total of from 2 to 15 carbon atoms, in some embodiments an alkyl diol or glycol which is reacted with an ether comprising an alkylene oxide having from 2 to 6 carbon atoms, typically ethylene oxide or propylene oxide or mixtures thereof. For example, hydroxyl functional polyether can be produced by first reacting propylene glycol with propylene oxide followed by subsequent reaction with ethylene oxide. Primary hydroxyl groups resulting from ethylene oxide are more reactive than secondary hydroxyl groups and thus are preferred. Useful commercial polyether polyols include poly(ethylene glycol) comprising ethylene oxide reacted with ethylene glycol, poly(propylene glycol) comprising propylene oxide reacted with propylene glycol. Suitable polyether polyols also include polyamide adducts of an alkylene oxide and can include, for example, ethylenediamine adduct comprising the reaction product of ethylenediamine and propylene oxide, diethylenetriamine adduct comprising the reaction product of diethylenetriamine with propylene oxide, and similar polyamide type polyether polyols. Copolyethers can also be utilized in the described compositions. Typical copolyethers include the reaction product of THF and ethylene oxide or THF and propylene oxide. These are available from BASF as Poly-THF® B, a block copolymer, and PolyTHF® R, a random copolymer. The various polyether intermediates generally have a number average molecular weight (Mn) as determined by assay of the terminal functional groups which is an average molecular weight greater than about 1450, such as from about 1,450 to about 8,000, or from about 1,450 to about 5,500, or from about 1,450 to about 3,000. In one embodiment, the include a PEG having an Mn of 8000. In some embodiments, the polyether intermediate includes a blend of two or more different molecular weight polyethers, such as a blend of 300 Mn and 1,450 Mn PEG or a blend of 1450 Mn and 8,000 Mn PEG.

The polyol component, when present, may include poly (ethylene glycol), poly(trimethylene oxide), ethylene oxide capped poly(propylene glycol), poly(hexamethylene carbonate) glycol, poly(pentamethylene carbonate) glycol, poly (trimethylene carbonate) glycol, dimer fatty acid based polyester polyols, or any combination thereof.

In some embodiments, the polyol component includes a polyether polyol. In some embodiments, the polyol component is essentially free of or even completely free of polyester polyols.

In some embodiments, the polyol component includes ethylene oxide, propylene oxide, butylene oxide, styrene oxide, poly(propylene glycol), poly(ethylene glycol), copolymers of poly(ethylene glycol) and poly(propylene glycol), epichlorohydrin, and the like, or combinations thereof. In some embodiments the polyol component includes poly (ethylene glycol).

The polyol component, in some embodiments, may include a multi-block polyol. The multi-block polyol can include combinations of polyether with polyester, for example, polyethylene oxide polyether (PEO)-polycaprolactone (PCL)) or (PCL-PEO-PCL) which give good control over hydrophilicity, degradation and mechanical properties. The use of multiblock polyether products PEO-PPO (polypropylene oxide-PEO better known as Pluronics® (a registered trademark of BASF Corporation) and block polyester such as PCL-PEO-PPO-PEO-PCL may also be used. It is also contemplated that alternative ester and ether blocks may be used, for example, multiblock polyethers in combination with a block polyester.

The Optional Chain Extender Component

The TPU compositions described herein can further include c) a chain extender component. Chain extenders include diols, diamines, and combination thereof.

Suitable chain extenders include relatively small polyhydroxy compounds, for example lower aliphatic or short chain glycols having from 2 to 20, or 2 to 12, or 2 to 10 carbon atoms. Suitable examples include ethylene glycol, diethylene glycol, propylene glycol, dipropylene glycol, 1,4-butanediol (BDO), 1,6-hexanediol (HDO), 1,3-butanediol, 1,5-pentanediol, neopentylglycol, 1,4-cyclohexanedimethanol (CHDM), 2,2-bis[4-(2-hydroxyethoxy) phenyl] propane (HEPP), hexamethylenediol, heptanediol, nonanediol, dodecanediol, 3-methyl-1,5-pentanediol, ethylenediamine, butanediamine, hexamethylenediamine, and hydroxyethyl resorcinol (HER), and the like, as well as mixtures thereof. In some embodiments the chain extender includes BDO, HDO, 3-methyl-1,5-pentanediol, or a combination thereof. In some embodiments, the chain extender includes BDO. Other glycols, such as aromatic glycols could be used, but in some embodiments the TPUs described herein are essentially free of or even completely free of such materials.

In some embodiments, the chain extender used to prepare the TPU is substantially free of, or even completely free of, 1,6-hexanediol. In some embodiments, the chain extender used to prepare the TPU includes a cyclic chain extender. Suitable examples include CHDM, HEPP, HER, and combinations thereof. In some embodiments, the chain extender used to prepare the TPU includes an aromatic cyclic chain extender, for example HEPP, HER, or a combination thereof. In some embodiments, the chain extender used to prepare the TPU includes an aliphatic cyclic chain extender, for example CHDM. In some embodiments, the chain extender used to prepare the TPU is substantially free of, or even completely free of aromatic chain extenders, for example aromatic cyclic chain extenders. In some embodiments, the chain extender used to prepare the TPU is substantially free of, or even completely free of polysiloxanes.

In some embodiments, the chain extender component includes 1,4-butanediol, 2-ethyl-1,3-hexanediol, 2,2,4-trimethyl pentane-1,3-diol, 1,6-hexanediol, 1,4-cyclohexane dimethylol, 1,3-propanediol, 3-methyl-1,5-pentanedio, diethylene glycol or combinations thereof. In some embodiments, the chain extender component includes 1,4-butanediol, 3-methyl-1,5-pentanediol or combinations thereof. In some embodiments, the chain extender component includes 1,4-butanediol. When present, the chain extender component can be utilized in an amount from 0.4 wt % to about 4.0 wt %.

Additional TPU Components

In some embodiments, the TPU described herein will further include an optional chain terminating agent. Chain terminating agents are well known and may be a monohydroxyl or mono primary amine or any other mono function compound that reacts with a di-isocyanate to terminate the step growth polymerization at the end of the polymerchain. These may be the same or different on either end of the polymer. The chain terminating agent may have a number average molecular weight ranging from 100 to 8000, linked to the polymer via a urethane or urea bond.

Examples of chain terminating agents include mono amine- or mono alcohol-terminated polyalkylene oxides, silicones, alkyl, alkylesters, polyalkylene esters and mixtures thereof. In some embodiments, a chain terminating group that may be used in the polyurethane copolymers according to the present invention include monofunctional polyethylene oxides, monofunctional polytetramethylene oxides, monofunctional polypropylene oxides, monofunctional siloxanes, and mixtures and/or copolymers thereof. Dodecylamines, alkoxylated alcohols such as cetereth-20, steareth 20 and the like. In one embodiment, the amount of chain terminating agent is from 0 wt %-2 weight % based on the total weight of the dry polyurethane copolymer.

The composition described herein is generally formed by dispersing a crosslinked poly(acrylic) acid polymer into water. The amount of the crosslinked poly(acrylic) acid polymer is, in one embodiment, from about 0.01 wt % to about 2.5 parts by weight and in another embodiment, from about 0.05 wt % to about 1.5 wt %, and in another embodiment from about 0.1 wt % to about 1.0 wt % for every 100 parts by weight of water. The hydrophilic TPU polymer is dissolved, in one embodiment, in water mixture in an amount of from about 0.01 wt % to about 2.5 wt % and in another embodiment from about 0.05 wt % to about 1.5 wt %, and in another embodiment from about 0.1 wt % to about 1.0 wt % for every 100 parts by weight of water.

It has been found that the degree of neutralization of the poly(acrylic) acid polymer has a direct impact on preparation of the blended poly(acrylic) acid polymer and TPU as well as the final hydrogel properties. Accordingly, in one embodiment, prior to blending of the two polymers, the poly(acrylic) acid polymer is partially neutralized from an initial pH of from about 2.0 up to about 8.0 or from about 2.0 up to about 6.5 or from about 2.0 up to about 4.0. In another embodiment, the TPU and the base to neutralize the poly(acrylic) acid polymer are blended. The poly(acrylic) acid polymer is then dispersed into In one embodiment the amount of neutralizer used is from 25% to 50% of the theoretical value necessary to achieve a polymer solution of pH 7. In another embodiment, the amount of neutralization is from 10% to 75% of the acid content of the polymer. In a still further embodiment, the pH of the polymer solution is from 4 to 8. Neutralization can be carried out with any convenient neutralizing agent or compound such as ammonium hydroxide, sodium hydroxide, other alkali hydroxides, borates, phosphates, pyrophosphates or polyphosphates; an amino acid, such as arginine; AMP-95 (2-Amino-2-Methyl-1-Propanol) a product of Angus Chemical, cocamine, oleamine, diisopropanolamine, diisopropylamine, dodecylamine, PEG-15 cocoamine, morpholine, tetrakis(hydroxypropyl) ethylenediamine, triamylamine, triethanolamine, triethylamine, or tromethamine (2-Amino 2-Hydroxymethyl-1,3-propanediol). In some embodiments, neutralizing agents include NaOH, tetrakis(hydroxypropyl)ethylenediamine, triethanolamine, and tromethamine.

The poly(acrylic) acid polymer and hydrophilic TPU are then blended together. In one embodiment, the ratio, by weight, of poly(acrylic) acid polymer to hydrophilic TPU is from 1:9 to 2:1, and in another embodiment from 1:3 to 1:1. Optionally, additional water or other solvent such as alcohols, polyols, or polyalkoxides can be added. Such additional water or solvent is dependent upon the desired final qualities and physical constraints of individual formulations.

In some embodiments, the hydrogels disclosed herein may be sterilized. Sterilization is the treatment process that rids materials of possible contaminants, including microbial life, bacteria, fungi and viruses. In order to limit transmission of these contaminants, the medical industry requires certain levels of sterilization. Several sterilization methods may be used. In one embodiment, sterilization may be conducted by immersing the product in ethylene oxide gas in a chamber, then aerating it. In another embodiment, the product is put in a sterilization chamber that is vacuumed and filled with hydrogen peroxide vapor and then aerated. Sterilization involving ionizing energy that has low penetration and uses a high dose rate to eliminate contaminants may be used. An accelerator produces a beam of electrons that are focused on the product to be sterilized. Sterilization using an isotope source, usually Cobalt-60, to produce ionizing energy that flows through the product may also be used. This energy causes cellular damage to the organisms, ridding the product of them. Sterilization utilizing hot air, conducting heat through the equipment may be used. Objects are heated to a steady temperature and held for a certain length of time, depending on the material. Dry heat sterilization is very effective, as it can reach all surfaces of an assembled product.

The gel as described herein can be utilized in various forms, including lotions, sprays, spray gels, compressed liquids, liquid suspensions, and the like.

The applied substance can be any material known, purported, or thought to have a beneficial effect on the chosen substrate, such as the substances listed in the preceding paragraph. While water-soluble active ingredients are most easily incorporated, the use of non-water carriers, emulsifiers, dispersed organic (hydrocarbon) phases, etc., can allow the delivery of nonpolar compounds (e.g., hydrocarbon materials such as aliphatic and aromatic compounds).

One class of substances are the therapeutic aids which include, but are not limited to, moisturizers (or things that help the substrate (skin) retain water); oils (or things that help the skin retain oil); pharmaceutical agents; antimicrobial agents; antibacterial agents; fungicide; anti-inflammatory/analgesic agents (e.g., things that reduce irritation); softening agents; toughening agents; agents that enhance elasticity of the substrate; agents that promote cell growth or cell reproduction; agents that retard cell growth or cell reproduction; stimulants for the cells or nerves, antihistamines; local anesthetics; and the like.

The hydrogel may include one or more active ingredients with one or more of the following advantages: sustained delivery, consistency in dosage, enhanced delivery, dosage control, efficiency, and bioavailability for: wound healing, burn healing, scar reducing, etc.; skin or keratin color changes (lightening, darkening, coloring), applying decorative images, highlighting; enhancing penetration of another active ingredient or medicine through the skin or other substrate; altering the fragrance or aroma of the substrate, or enhancing fat, e.g., cellulite reduction; applying a hormone, steroid, or pheromone, etc.

The active ingredient may be of any polarity from low to high including fragrances, coloring, pigments, ointments, etc. Where desired, water solubility may be enhanced by the addition of other carriers, additives, etc. In many embodiments, a mixture of two or more active ingredients which act independently or in conjunction with each other will be used. The active ingredient can be any of the following: a moisturizer, an anti-aging agent (removing aging effect or repairing aging effects); an astringent, an acid (e.g., glycolic, citric, and vitamins); a skin stimulator (e.g., menthol, camphor, and cayenne pepper extract); a firming agent; a slimming agent; a radical scavenger; solubilizers, an antihistamine (e.g., diphenhydramine or chlorpheniramine maleate); methyl salicylate; glycol salicylate; an aroma-therapeutic; a humectant; an emollient; a phytochemical (natural extract such as herbal and botanical e.g., bamboo, tea tree oil, etc.), an antioxidant, a skin whitening agent (e.g., hydroquinone, peroxide, and kojic acid); a self-tanning agent or agent for adding skin colorant (e.g., dihydroxy acetone); a skin protecting agent (e.g., moisturizers, waxes, sunblocks (organic or inorganic)); a spot remover (substrate may be people); keratin, retinol; vitamins; vitamin complexes; precursors of active ingredients such a precursors of retinol; salicylic acid and derivatives of salicylic acid; peptide; oligomeric and polymeric peptide; an enzyme; a coenzyme; proteins and their precursors; amino acid (e.g., dimers, cyclic and aliphatic amino acid); glycosamineoglycans; saccharides; derivatives of saccharides; plysaccharides; oligomeric saccharides; cyclic oligomeric saccharides; carbohydrates, fatty acid triglycerides essential fatty acids; lipids; lecithin; phospholipids; conditioning agents; milk derivatives; carotenes; cyclodextrins; tocopherols; phytosterols; cationic agents; oil (natural such a animal and vegetable, synthetic including primrose oil, jojoba oil, mineral oil, castor oil, palm oil, coconut oil, corn oil, silicones, and derivatized forms thereof; gelatins, natural starch, modified starches, cellulosics and chemically modified cellulosics, sodium alginate, acacia, corn starch, cascin, natural gums, and/or modified natural gums; waxes (natural such a plant and synthetic); quaternized compounds; silicone and/or silicone derivatives;

protein hydrozylates or derivative proteins; chitin; denatured chitin; chitosan; marine derived compounds or marine origin materials (e.g. anything from the sea including things such as kelp, coral, seawood, marine moisturizing factor, algae, sea plants, phytoplankton, kelp, and their extracts); hydrolyzed animal and/or vegetable protein; astringent (e.g. zinc oxide, tannic acid, alum, aluminum sulfate, vitamin, dl-α-tocopherol); a wetting agent; a water repellant; an antimicrobial; a deodorant; a fungicide; a fruit acid; nut extracts/oils; a fragrance; flower acids; ceramides; a flavonoid; biologically derived materials (biotechnology); sodium hyaluronate; hyaluronic acid; etc.

In one embodiment, the clarity and/or appearance of the hydrogels of the invention can be adjusted. The clarity of the hydrogels may vary from substantially transparent, with little visual haze, to where insoluble component additives such as beads, air bubbles, pearlizing agents, are clearly visible to visually opaque. The hydrogels may incorporate long-term suspension of particles, insoluble liquid droplets, or the stabilization of gas bubbles within the medium. The materials or compounds which may be suspended can be soluble or insoluble. In some embodiments, the hydrogel is opacified by deliberately incorporating pearlescent materials therein to achieve an attractive pearl-like appearance, known as pearlescence. Examples of such other insoluble compounds include pigments, minerals such as bismuth, antimicrobials such as silver or zinc particles, dyes, and the like.

Visually distinct, multiple phase compositions where one phase is clear and another phase is opaque are also envisioned. In one embodiment of the invention, a pattern comprising phases that are visually distinct from each other may be formed by mixing clear and opaque components. The visual distinction between each phase can be in color, texture, density, and the type of insoluble component or benefit agent contained therein. The specific pattern can be chosen from a wide variety of patterns.

Gel Properties

The choice of the TPU component, and the ratio between the poly(acrylic) acid polymer and the TPU component, as well as the degree of neutralization of the poly(acrylic) acid polymer will each have an impact on the physical properties of the resulting hydrogel. These parameters may be used to select the combination of the properties desired in the resulting hydrogel. By way of example, the physical properties may include one or more of the following: viscosity, yield stress, salt response. A few of the more important physical properties are further commented on below.

Viscosity can be determined according to Brookfield viscosity. In some embodiments, the viscosity of the hydrogel will be from about 3,000 Cps to 200,000 mPa*s, and in another embodiment, from 3,000 to 150,000 mPa*s, or from 3,000 to 120,000 mPa*s, as tested by Brookfield rotating spindle method at 20 RPM.

Figure 1:
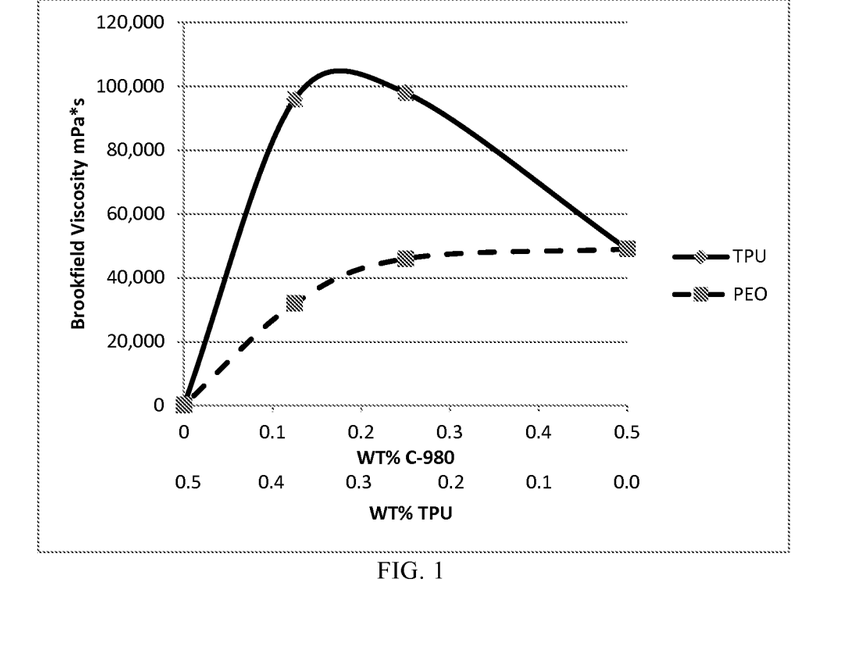
FIG. 1 is a graphical illustration of the viscosity profiles of hydrogel compositions of the invention compared with blends of a cross-linked poly(acrylic) acid with conventional polyethylene oxide at constant polymer concentrations with increasing content of poly(acrylic) acid.

Referring to FIG. 1, there is illustrated the synergistic effect with respect to viscosity obtained with the inventive hydrogel of crosslinked polyacrylic acid and TPU compared to the lack of synergy between crosslinked polyacrylic acid and high molecular weight polyethylene oxide (PEO). As can be seen, the inventive hydrogel provides an increased viscosity profile as compared with the crosslinked polyacrylic acid and high molecular weight polyethylene oxide (PEO).

Figure 2:
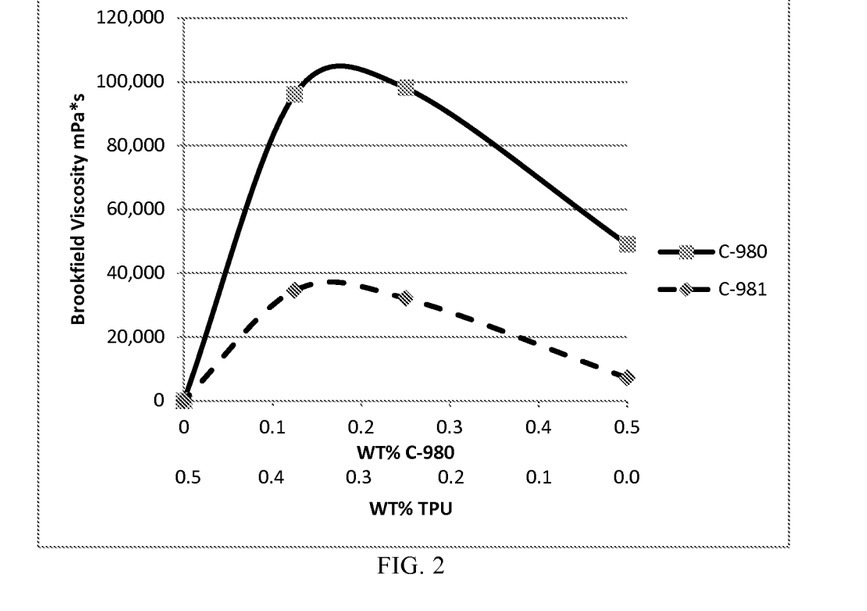
FIG. 2 is a graphical illustration of the viscosity profiles of hydrogels according to the invention at constant polymer concentration utilizing two different cross-linked polyacrylic acid formulations.

FIG. 2 further illustrates the synergy in Brookfield Viscosity at 20 RPM in the inventive hydrogel containing a higher viscosity crosslinked polyacrylic acid with thermoplastic polyurethane (solid line) and a lower viscosity crosslinked polyacrylic acid with thermoplastic polyurethane (dotted line) at 1.0 wt % total polymer, with increasing percentage of crosslinked polyacrylic acid. Both high viscosity and low viscosity crosslinked polyacrylic acid show higher viscosity when blended with the thermoplastic polyurethane.

Yield Stress and shear response can be determined according to microviscosity by estimated fitting to the Casson rheological model or rheology. In some embodiments, the shear response of the hydrogel will be from about 130 mPa*s to about 1,000 mPa*s, and in another embodiment from about 215 mPa*s to about 1,000 mPa*s.

Yield stress and shear response may also be determined via the Brookfield method, as set forth hereinafter in the Examples.

Salt response can be determined according to Brookfield viscosity measured at 1 wt % of the hydrogel composition and 1 wt % of sodium chloride at 20 RPM. In some embodiments the salt response of the hydrogel will be from about 325 mPa*s to about 50,000 mPa*s.

Shear thinning behavior of a power law fluid can be determined utilizing Brookfield viscosity at different speeds. Viscosity is plotted against spindle speed to show relationships of the form:

$$y=ax^k,$$

with the power term k corresponding to slope, which represents the shear thinning of the sample as measured by Brookfield viscosity and may be referred to as the flow behavior index (a dimensionless number). Where k is less than one, the power law predicts that the effective viscosity would decrease with increasing shear rate.

Industrial Application

Some embodiments of the invention relate to the use of the hydrogels as multi-functional polymer ingredients in personal care, health care, household, institutional and industrial product applications and the like. The hydrogels can be employed as emulsifiers, spreading aids and carriers for enhancing the efficacy, deposition and delivery of chemically and physiologically active ingredients and cosmetic materials, and as a vehicle for improving the psychosensory and aesthetic properties of a formulation in which they are included. The term "personal care products" as used herein includes, without limitation, cosmetics, toiletries, cosmeceuticals, beauty aids, personal hygiene and cleansing products that are applied to the skin, hair, scalp, and nails of humans and animals. The term "health care products" as used herein includes, without limitation, pharmaceuticals, pharmacosmetics, oral care products (mouth, teeth), eye care products, ear care products and over-the-counter products and appliances, such as patches, plasters, dressings and the like. The term also includes medical devices that are externally applied to or into the body of humans and animals for ameliorating a health related or medical condition. The term "body" includes the keratinous (hair, nails) and non-keratinous skin areas of the entire body (face, trunk, limbs, hands and feet), the tissues of body openings and the eyes. The term "skin" includes the scalp and mucous membranes.

The hydrogels of the invention are suitable for personal care (cosmetics, toiletries, cosmeceuticals) and topical health care products, including, without limitation, skin care products (facial, body, hands, scalp and feet), such as creams, lotions and cleansing products, antiacne products, antiaging products (exfoliant, keratolytic, anticellulite, antiwrinkle, and the like), skin protectants (sun care products, such as sunscreens, sunblock, barrier creams, oils, silicones and the like), skin color products (whiteners, lighteners, sunless tanning accelerators and the like), bath and shower products (body cleansers, body wash, shower gel, liquid soap, conditioning liquid bath oil, bubble bath, and the like).

Topical health and beauty aids can include the hydrogels of the invention as spreading aids and film formers include, without being limited thereto, skin protective sprays, cream, lotion, gels, such as insect repellants, itch relief, antiseptics, disinfectants, sun blocks, sun screens, skin tightening and toning milk and lotions, wart removal compositions, and the like.

The hydrogels of the invention may find use as suspending agents for particulates making them suitable for dermal products containing particulates, microabrasives, and abrasives, such as shower gels, masks and skin cleansers containing exfoliative scrubs agents. Typical particulates include, but are not limited thereto, shell, seed, and stone granules, such as almonds, apricot (seed, kernel powder, shell), avocado, coconut, corn cob, olive, peach, rose hip seed, walnut shell, and the like, aluminum silicate, jojoba (wax, seed powder), oyster shell powder, evening primrose seed, milled adzuki beans, and the like, polyethylene (granules, spheres), polyethylene (and) hydroxycellulose granules, microcrystalline cellulose, polystyrene, polystyrene (and) talc granules, ground pumice, ground loofah, ground seaweed, rice, oat bran, silica (hydrated, colloidal, and the like), ground eggshell, ground blue poppy seed, salt, such as sodium chloride, dead sea salt, and the like, and mixtures thereof.

The hydrogels of the invention are useful as thickeners and film formers in a variety of dermatological, cosmeceutical compositions employed for topically ameliorating skin conditions caused by aging, drying, photodamage, acne, and the like, containing conditioners, moisturizers, antioxidants, exfoliants, keratolytic agents, vitamins, and the like. The hydrogels of the invention can be employed as a thickener for active skin treatment lotions and creams, containing as such active ingredients, acidic anti-aging agents, anti-cellulite, and anti-acne agents, such as alpha-hydroxy acid (AHA), beta-hydroxy acid (BHA), alpha amino-acid, alpha-keto acids (AKAs), and mixtures thereof. In such cosmeceuticals, AHAs can include, but are not limited to, lactic acid, glycolic acid, fruit acids, such as malic acid, citric acid, tartaric acid, extracts of natural compounds containing AHA, such as apple extract, apricot extract, and the like, honey extract, 2-hydroxyoctanoic acid, glyceric acid (dihydroxypropionic acid), tartronic acid (hydroxypropanedioic acid), gluconic acid, mandelic acid, benzilic acid, azelaic acid, acetic acid, alpha-lopioc acid, salicylic acid, AHA salts and derivatives, such as arginine glycolate, ammonium lactate, sodium lactate, alpha-hydroxybutyric acid, alpha-hydroxyisobutyric acid, alpha-hydroxyisocaproic acid, alpha-hydroxyisovaleric acid, atrolactic acid, and the like. BHAs can include, but are not limited to, 3-hydroxypropanoic acid, beta-hydroxybutyric acid, beta-phenyl lactic acid, beta-phenylpyruvic acid, and the like. Alpha-amino acids include, without being limited to, alpha-amino dicarboxylic acids, such as aspartic acid, glutamic acid, and mixtures thereof, sometimes employed in combination with fruit acids. AKAs include pyruvic acid. In some antiaging compositions, the acidic active agent may be retinoic acid, a halocarboxylic acid, such as trichloroacetic acid, an acidic antioxidant, such as ascorbic acid (vitamin C), a mineral acid, phytic acid, lysophosphatidic acid, and the like. Some antiacne agents, for example, can include salicylic acid, derivatives of salicylic acid, such as 5-octanoylsalicylic acid, retinoic acid and its derivatives.

Other health care products in which the hydrogels of the invention can find use are medical products, such as topical and non-topical pharmaceuticals and devices. In the formulation of pharmaceuticals, a hydrogel of the invention can be used as a thickener and/or lubricant in such products as binders, coatings, controlled release agents, creams, pomades, gels, pastes, ointments, gel capsules, purgative fluids (enemas, emetics, colonics, and the like), suppositories, anti-fungal foams, eye products (ophthalmic products such as eyedrops, artificial tears, glaucoma drug delivery drops, contact lens cleaner, and the like), ear products (wax softeners, wax removers, otitis drug delivery drops, and the like), nasal products (drops, ointments, sprays, and the like), wound care (liquid bandages, wound coverings, antibiotic creams, ointments and the like), and burn gels, without limitation thereto.

The amount of each chemical component described is presented exclusive of any solvent, which may be customarily present in the commercial material, that is, on an active chemical basis, unless otherwise indicated. However, unless otherwise indicated, each chemical or composition referred to herein should be interpreted as being a commercial grade material which may contain the isomers, by-products, derivatives, and other such materials which are normally understood to be present in the commercial grade.

It is known that some of the materials described above may interact in the final formulation, so that the components of the final formulation may be different from those that are initially added. For instance, metal ions (of, e.g., a detergent) can migrate to other acidic or anionic sites of other molecules. The products formed thereby, including the products formed upon employing the composition of the present invention in its intended use, may not be susceptible of easy description. Nevertheless, all such modifications and reaction products are included within the scope of the present invention; the present invention encompasses the composition prepared by admixing the components described above.

EXAMPLES

The invention will be further illustrated by the following examples, which sets forth particularly advantageous embodiments. While the examples are provided to illustrate the present invention, they are not intended to limit it. Unless otherwise specified weight percents (wt. %) are given in wt. % based on the weight of the total composition.

Test Methods

Brookfield rotating spindle method (Most viscosity measurements reported herein are conducted by the Brookfield method unless specifically described as by Physica Rheolab MC100 rheometer method): The viscosity measurements are calculated in centapoise (cPs or mPas), employing a Brookfield rotating spindle viscometer, Model RVT (Brookfield Engineering Laboratories, Inc.), at about 20 revolutions per minute (rpm), at ambient room temperature of about 20 to 25° C. (hereafter referred to as viscosity). Spindle sizes are selected in accordance with the standard operating recommendations from the manufacturer. Generally, spindle sizes are selected as follows:

| Spindle Size No. | Viscosity Range (Cps) |
| --- | --- |
| 1 | 1-50 |
| 2 | 500-1,000 |
| 3 | 1,000-5,000 |
| 4 | 5,000-10,000 |
| 5 | 10,000-20,000 |
| 6 | 20,000-50,000 |
| 7 | >50,000 |

The spindle size recommendations are for illustrative purposes only. The artisan of ordinary skill in the art will select a spindle size appropriate for the system to be measured. Brookfield Yield Value (Stress) determination method as reported in Lubrizol document TDS-244—Measurement and Understanding of Yield Value. A Brookfield RVT viscometer is used to measure the torque necessary to rotate a spindle through a liquid sample at speeds of 0.5 to 100 rpm. Multiplying the torque reading by the appropriate constant for the spindle and speed gives the apparent viscosity. Spindle speed corresponds to shear rate. Yield value is an extrapolation of measured values to a shear rate of zero. Brookfield yield value (BYV) can be calculated by the following if spindle speeds of 0.5 and 1 rpm are used:

$$BYV, \text{dyn/cm2} = \frac{(\eta \alpha 1 - \eta \alpha 2)}{100} \text{ or } BYV, \text{Pa} = \frac{(\eta \alpha 1 - \eta \alpha 2)}{1000}$$

Rheological Measurements

A Physica Rheolab MC100 rheometer set up for torsional flow was used for the following measurements. The temperature of the measurement was 25 C and the gap was set at 0.050 mm on a 75 mm cone with a 1 angle. A linear ramp of 0-50 sec-1 in 300 sec was used for the forward and a linear decrease of 50-0 sec-1 in 300 sec was used. The shear rate was controlled and the shear stress calculated from the torque. A known mucilage of polymer as prepared in example is centrifuged to remove any bubbles. Sample mucilage is loaded on the bottom plate and excess is removed. The flow curve program is started and data collected under increasing levels of steady shear. The following information is generated with the last two properties obtained from Casson's model:

Viscosity is a function of shear rate $\eta(\gamma)\eta = \sigma/\gamma =$ shear stress/shear rate.

Thixotropic index: the area between the forward ramp curve and the return ramp curve according to the following equation:

$$Y^{1/p} = a + b\, X^{1/p}$$

where Y is shear stress, X is shear rate, and p equals 2;
Yield stress ρ (yield value, yield point) is the Y intercept (a); and
Limiting viscosity at high shear rates (microviscosity, η ∞b) is the slope.

Materials

The materials are generally commercially available from chemical supply houses known to those skilled in the chemical arts or from the supplier indicated below.

| | |
| --- | --- |
| Carbopol ® 980NF | Carbomer homopolymer Type C available from The Lubrizol Corporation |
| Carbopol ® 981 NF | Carbomer homopolymer Type A available from The Lubrizol Corporation |
| Carbopol ® Ultrez-10 NF | Carbomer interpolymer Type A available from The Lubrizol Corporation |
| Carbopol ® ETD 2020 | Carbomer Interpolymer Type B available from The Lubrizol Corporation |
| Euxyl-PE9010 | liquid preservative based on phenoxyethanol and ethylhexylglycerin available from Schülke, Inc. |
| Noveon ® PolyCarbophil AA-1 USP | Polycarbophil available from the Lubrizol Corporation |
| PolyOx WSR-301 | polyethylene oxide available from Colorcon having molecular weight of $1 \times 10^5$ to $7 \times 10^6$ |
| TPU1 | aliphatic polyether thermoplastic polyurethane available from The Lubrizol Corporation |
| TPU2 | aliphatic polyether thermoplastic polyurethane available from The Lubrizol Corporation |
| TPU3 | aliphatic polyether thermoplastic polyurethane available from The Lubrizol Corporation |

Preparation of Carbopol 980 NF (0.5 wt %) Masterbatch 497 gm DI water is placed in a 800 ml beaker and stirred with a Lightnin mixer at 1,000 rpm with a 3 blade marine impeller. 0.5 gm Euxyl-PE is added to the water and mixed. 2.5 gm Carbopol 980 NF is introduced through a 20 mesh screen with stirring and mixed for 20 minutes until thoroughly hydrated. The pH is recorded and 18 wt % NaOH in water is added until a final pH of 6.5+/−0.2 is achieved. The pH and Brookfield viscosity using a Brookfield RVT-DV viscometer at 20 rpm·s Preparation of Masterbatches of Carbopol® 980 NF, 981NF and ETD 2020NF Master batches of Carbopol 980NF, Carbopol 981NF and ETD 2020NF at the designated weight % as set forth in Table 1 are prepared in the same manner as described in Example 1. Data for each of the batches is presented in Table 1.

TABLE 1

Concentration, pH and Brookfield Viscosity of crosslinked polyacrylic acid baseline gels before and after neutralization.

| Sample Description | Sample# | Wt % Total Polymer | pH dispersion | Dispersion Brookfield viscosity | Neutralized pH | Neutralized Brookfield Viscosity (20 RPM) mPas | Brookfield Yield Stress (Pa) |
|---|---|---|---|---|---|---|---|
| Carbopol 980NF | Baseline-1A | 0.5 | 3.07 | 58 | 6.79 | 49,000 | 152 |
| | Baseline-2A | 1 | 2.9 | 1134 | 6.6 | 72,000 | 300 |
| | Baseline-3A | 1.5 | 2.76 | 2985 | 6.64 | 81,000 | 440 |
| Carbopol 981 NF | Baseline-1B | 0.5 | 3.07 | 58 | 6.7 | 7,120 | 49 |
| | Baseline-2B | 1 | 2.9 | 1134 | 6.62 | 10,960 | 73 |
| | Baseline-3B | 1.5 | 2.76 | 2985 | 6.78 | 14,300 | 100 |
| ETD2020NF | Baseline-1C | 0.5 | | | 6.78 | 23,750 | 184 |
| | Baseline-2C | 1 | | | 6.75 | 48,200 | 356 |
| | Baseline-3C | 1.5 | | | 6.84 | 80,000 | 560 |

Preparation of Masterbatch of TPU1

885.6 gm DI water is placed in a 1 l jar with a lid and stirred with a magnetic stirrer. 0.9 gm Euxyl-PE is added to the water and mixed. 13.5 gm TPU1 is added to the water and mixed until a smooth solution is achieved. The pH, and Brookfield viscosity at 20 rpm is measured.

Masterbatches of TPU1 at the designated weight % as set forth in Table 2 are prepared in the same manner as described in Example 2.

TABLE 2

Concentration, pH and Brookfield Viscosity of TPU baseline gels

| Sample Description | Sample # | Wt % | pH | Brookfield viscosity mPas 20 RPM | Neutralized Brookfield Yield Stress Pa |
|---|---|---|---|---|---|
| TPU1 | Baseline-4 | 0.5 | 6.12 | 11 | 0 |
| | Baseline-5 | 1 | 6.29 | 138 | 0 |
| | Baseline-6 | 1.5 | 6.36 | 2,125 | 0 |

Preparation of PolyOx 885.6 gm DI water is placed in a 1 l jar with a lid and stirred with a magnetic stirrer. 0.9 gm Euxyl-PE is added to the water and mixed. 13.5 gm Sentry PolyOx WSR 301 is added to the water and mixed until a smooth solution is achieved. The pH, and Brookfield viscosity at 20 rpm is measured.

Masterbatches of PolyOx WSR 301 at designated wt % are prepared in the same manner as above. Data is presented in Table 3.

TABLE 3

Concentration, pH and Brookfield Viscosity of Polyethylene Oxide PolyOx (PEO) baseline gels

| Sample Description | Sample # | Wt % | pH | Brookfield viscosity mPas 20 RPM | Brookfield Yield Stress Pa |
|---|---|---|---|---|---|
| Polyox WSR-301 | Baseline-7 | 0.5 | 9.17 | 118 | 0 |
| | Baseline-8 | 1 | 9 | 922 | 1 |
| | Baseline-9 | 1.5 | 9.09 | 3,250 | 5 |

Each of the Samples in Tables 1-3 indicate the viscosity of 100% solutions at the same concentrations. Both the TPU1 (Sample #s Baseline 4-6) and the PEO Polyox (Sample #s Baseline 7-9) have low viscosities at 0.5 wt % and 1 wt % and do not start to build any significant viscosity until above 1.5 wt %. In comparison, the Carbopol samples (Baseline #s 1-3) build viscosity at low concentrations of 0.5 wt % and 1 wt %.

Preparation of Blends of Carbopol 980NF and TPU1

The masterbatch 980-1 (100 gm) and masterbatch TPU1 (100 gm) and 200 gm of DI water are blended in a 800 ml beaker until smooth. The pH, and Brookfield viscosity at 20 rpm is measured.

Further blends of Carbopol 980NF and TPU1 at designated wt % are prepared in the same manner as above. Data for the concentration of baseline gels and water to prepare the final blend is presented in Table 4.

TABLE 4

Concentration of C-980 and TPU1 and water to prepare the inventive blends

| Sample # | Wt % Total Polymer | Wt % 980 | Wt % TPU1 | Baseline-1A (g) | Baseline 4 (g) | DI H2O (g) |
|---|---|---|---|---|---|---|
| Inventive 1 | 0.25 | 0.125 | 0.125 | 100 | 100 | 200 |
| Inventive 2 | 0.50 | 0.25 | 0.25 | 200 | 200 | |
| Inventive 3 | 0.50 | 0.125 | 0.38 | 100 | 300 | |
| Inventive 4 | 0.25 | 0.06 | 0.19 | 50 | 150 | 200 |
| | | | | Baseline 3A (g) | Baseline 6(g) | |
| Inventive 5 | 1.50 | 0.38 | 1.12 | 167 | 500 | |

Blend of Carbopol 980-1 and PolyOx WSR 301

The Masterbatch 980-1 (100 gm) and master batch PolyOx-1 (100 gm) and 200 gm of DI water are blended in a 800 ml beaker until smooth. The pH, and Brookfield viscosity at 20 rpm is measured.

Blends of Carbopol 980 and PolyOx WSR 301 at designated wt % are prepared in the same manner as above. Data for the concentration of baseline gels and water to prepare the comparative blends are presented in Table 5.

TABLE 5

Concentration of C-980 and PEO PolyOx and water to prepare the comparative blends

| Sample # | Wt % Total Polymer | Wt % 980 | Wt % PolyOx | Baseline 1A (g) | Baseline 7 (g) | DI H2O (g) |
|---|---|---|---|---|---|---|
| Comparative 1 | 0.25 | 0.125 | 0.125 | 100 | 100 | 200 |
| Comparative 2 | 0.50 | 0.25 | 0.25 | 200 | 200 | |

TABLE 5-continued

Concentration of C-980 and PEO PolyOx and water to prepare the comparative blends

| Sample # | Wt % Total Polymer | Wt % 980 | Wt % PolyOx | Baseline 1A (g) | Baseline 7 (g) | DI H2O (g) |
|---|---|---|---|---|---|---|
| Comparative 3 | 0.50 | 0.125 | 0.38 | 100 | 300 | |
| Comparative 4 | 0.25 | 0.06 | 0.19 | 50 | 150 | 200 |
| | | | | Baseline 3A (g) | Baseline 6 (g) | |
| Comparative 5 | 1.50 | 0.38 | 1.12 | 167 | 500 | |

Hydrogel compositions of the invention using the same baseline gels of Carbopol 981 and ETD 2020 are blended with baseline gels of TPU1 in a similar manner.

TABLE 6

Concentration and Brookfield viscosity data for the baseline, inventive, and comparative gels

| | Wt % Total Polymer | Carbopol | PolyOx | TPU1 | Brookfield Viscosity (20 rpm) mPa · s | Yield Value Brookfield Pas | Shear Response Brookfield |
|---|---|---|---|---|---|---|---|
| Baseline 1A | 0.5 | 0.5 | | | 49,000 | 152 | −0.598 |
| Baseline 2A | 1 | 1 | | | 72,000 | 300 | −0.684 |
| Baseline 3A | 1.5 | 1.5 | | | 81,000 | 440 | −0.759 |
| Baseline 4 | 0.5 | | | 0.5 | 11 | 0 | |
| Baseline 5 | 1 | | | 1 | 138 | 0 | 0.0073 |
| Baseline 6 | 1.5 | | | 1.5 | 2,125 | 0.01 | 0.0183 |
| Baseline 7 | 0.5 | | 0.5 | | 118 | 0.02 | −0.209 |
| Baseline 8 | 1 | | 1 | | 922 | 0.96 | −0.41 |
| Baseline 9 | 1.5 | | 1.5 | | 3,250 | 5.4 | −0.518 |
| Inventive 1 | 0.25 | 0.125 | | 0.125 | 50,800 | 506 | −0.848 |
| Inventive 2 | 0.5 | 0.25 | | 0.25 | 98,000 | 970 | −0.875 |
| Inventive 3 | 0.5 | 0.125 | | 0.38 | 96,000 | 920 | −0.874 |
| Inventive 4 | 0.25 | 0.06 | | 0.19 | 22,250 | 145 | −0.757 |
| Inventive 5 | 1.5 | 0.38 | | 1.12 | 194,000 | 2,400 | −0.853 |
| Comparative 1 | 0.25 | 0.125 | 0.125 | | 34,000 | 104 | −0.708 |
| Comparative 2 | 0.5 | 0.25 | 0.25 | | 46,000 | 188 | −0.76 |
| Comparative 3 | 0.5 | 0.125 | 0.38 | | 32,000 | 136 | −0.767 |
| Comparative 4 | 0.25 | 0.06 | 0.19 | | 13,660 | 86 | −0.758 |
| Comparative 5 | 1.5 | 0.38 | 1.12 | | 40,000 | 308 | −0.829 |

As can be seen in Table 6, the Brookfield viscosity at 20 RPM illustrates the increase in viscosity, indicating a synergy between high viscosity Carbopol 980 and TPU1 as compared to the Carbopol 980 and PolyOx blend. This is further illustrated in FIG. 1 which shows the increase in viscosity for the inventive blend over the baseline gels and the comparative blend at the same total polymer concentration.

Table 6 also illustrates the Yield value in Pas as measured by Brookfield for the baseline polymers 4 through 9, indicating that these polymer solutions have little to no ability to suspend, and the inventive polymers 1-5 show higher yield value than the comparative and baseline at the same polymer concentrations.

The Shear Response as measured by Brookfield, which is also referred to as the flow behavior index, is shown in Table 6. For Baseline 4, 5 and 6 the number is very small, indicating that there is very little slope to the line. The polyethylene oxide baseline 7, 8, 9 is also shear thinning, which is well known. It is shown in the inventive polymer that the shear response as measured by Brookfield is greater for the inventive polymers than the comparative polymers, which are a combination of two shear thinning polymers.

Preparation of Masterbatches of Polycarbophil

Master batches of Polycarbophil (Baseline 1D, 2D, and 3D) at the designated weight % as set forth in Table 9 are prepared in the same manner as described above. Data for each of the batches is presented in Table 9.

TABLE 7

Concentration and Brookfield viscosity data for Carbopol 980 baseline, inventive, and comparative gels

| | Wt % Total Polymer | Carbopol 980 | PolyOx | TPU1 | Brookfield Viscosity (20 rpm) mPa*s | Brookfield Yield Stress Pa |
|---|---|---|---|---|---|---|
| Baseline 1A | 0.5 | 0.5 | | | 49,000 | 152 |
| Inventive 2 | 0.50 | 0.25 | | 0.25 | 98,000 | 970 |
| Comparative 2 | 0.50 | 0.25 | 0.25 | | 46,000 | 104 |
| Baseline 1C | 1.5 | | | | 41,000 | 440 |
| Inventive 5 | 1.5 | 0.38 | | 1.12 | 194,000 | 2,400 |
| Comparative 5 | 1.5 | 0.38 | 1.12 | | 40,000 | 308 |
| Inventive 1 | 0.25 | 0.125 | | 0.125 | 50,800 | 506 |
| Comparative 1 | 0.25 | 0.125 | 0.125 | | 34,000 | 104 |
| Inventive 3 | 0.50 | 0.125 | | 0.38 | 96,000 | 920 |
| Comparative 3 | 0.50 | 0.125 | 0.38 | | 32,000 | 136 |

As can be seen in the above Table 7, the addition of TPU1 to Carbopol 980NF increases the Brookfield viscosity at 20 RPM, while the addition of Polyox to Carbopol does not increase viscosity. Further, in the comparative samples 1 and 3, it can be seen that Carbopol is the major contributor to the viscosity profile and not the Polyox as the viscosity of these samples are essentially the same, even though the amount of Polyox was increased.

Table 7 further illustrates the comparison of the Brookfield Yield Stress of the inventive polymers over the comparative polymers of the same concentrations.

TABLE 8

Concentration and Brookfield viscosity data for low viscosity Carbopol 981 baseline and inventive gels

| | Wt % Total Polymer | Wt % Carbopol 981 | Wt % TPU1 | Brookfield Viscosity (20 rpm) mPa*s |
|---|---|---|---|---|
| Baseline 1B | 0.5 | 0.5 | | 7,120 |
| Baseline 2B | 1 | 1 | | 10,960 |
| Baseline 3B | 1.5 | 1.5 | | 14,300 |
| Baseline 4 | 0.5 | | 0.5 | 11 |
| Baseline 5 | 1 | | 1 | 138 |
| Baseline 6 | 1.5 | | 1.5 | 2,125 |
| Inventive 6 | 0.25 | 0.125 | 0.125 | 8,960 |
| Inventive 7 | 0.50 | 0.25 | 0.25 | 32,100 |
| Inventive 8 | 0.50 | 0.125 | 0.38 | 34,600 |
| Inventive 9 | 0.25 | 0.06 | 0.19 | 16,700 |
| Inventive 10 | 1.5 | 0.38 | 1.12 | 70,000 |

As can be seen in Table 8, the Brookfield viscosity at 20 RPM illustrates the viscosity and shear response data indicating a synergy between low viscosity Carbopol 981NF and TPU1. FIG. 2 shows that a similar increase in viscosity is seen for the blends of high viscosity crosslinked carbomer and low viscosity carbomer with TPU1 at constant total polymer concentration of 1 wt %.

Preparation of Masterbatches of Carbopol® Ultrez-10 NF

Master batches of Carbopol Ultrez-10NF (Baseline 1E, 2E, and 3E) at the designated weight % as set forth in Table 9 are prepared in the same manner as described above. Data for each of the batches is presented in Table 9.

TABLE 9

| Sample Description | Wt % Total Polymer | Neutralized pH | Neutralized Brookfield Viscosity (20 RPM) Pa*2 | Yield value (stress) Brook field Pa |
|---|---|---|---|---|
| Baseline 1D | 0.5 | 5.12 | 14300 | 91.6 |
| Baseline 2D | 1 | 4.94 | 24250 | 120 |
| Baseline 3D | 1.5 | 4.97 | 32250 | 546 |
| Baseline 1E | 0.5 | 5.11 | 45,300 | 80 |
| Baseline 2E | 1 | 5.02 | 78,800 | 216 |
| Baseline 3E | 1.5 | 5.01 | 116600 | 748 |

Preparation of Blends of Polycarbophil and TPU1

200 g of the masterbatch 0.5 wt % TPU1 (Baseline 4) and 77 g of 18 wt % NaOH are blended. 200 g of 0.5 wt % polycarbophil acid dispersion is added. The solution is stirred until homogeneous. The pH and Brookfield viscosity at 20 rpm is measured.

Further blends of polycarbophil dispersions and TPU1 (Baseline 4, 5 and 6) at designated weight percent are prepared in the same manner as above. Data for the concentration of baseline gels and water to prepare the final blend is presented in Table 10.

TABLE 10

Concentration of Polycarbophil/Ultrez10 and TPU1 and water to prepare inventive blends

| Sample # | Wt % Total Polymer | Wt % Polycarbophil | Wt % TPU1 | Polycarbophil | gm | TPU1-1 | gm | NaOH 18 wt % gm |
|---|---|---|---|---|---|---|---|---|
| Inventive 11 | 0.5 | 0.25 | 0.25 | Baseline 1D | 200 | Baseline 4 | 200 | 0.77 |
| Inventive 12 | 1 | 0.5 | 0.5 | Baseline 2D | 200 | Baseline 5 | 200 | 1.54 |
| Inventive 13 | 1 | 0.25 | 0.75 | Baseline 3D | 133.3 | Baseline 6 | 266.7 | 1 |

| Sample # | Wt % Total Polymer | Wt % Carbomer interpolymer | Carbomer interpolymer | | | | | |
|---|---|---|---|---|---|---|---|---|
| Inventive 14 | 0.5 | 0.25 | 0.25 | Baseline 1E | 200 | Baseline 4 | 200 | 0.77 |
| Inventive 15 | 1 | 0.5 | 0.5 | Baseline 2E | 200 | Baseline 5 | 200 | 1.54 |
| Inventive 16 | 1 | 0.25 | 0.75 | Baseline 3E | 133.3 | Baseline 6 | 266.7 | 0.77 |
| Inventive 17 | 0.5 | 0.25 | 0.25 | Baseline 1C | 200 | Baseline 4 | 200 | 0.7 |
| Inventive 18 | 1 | 0.25 | 0.75 | Baseline 2C | 100 | Baseline 5 | 300 | 1.5 |
| Inventive 19 | 1.5 | 0.5 | 1 | Baseline 3C | 150 | Baseline 6 | 300 | 1.64 |

TABLE 11

Concentration and Brookfield viscosity data for Polycarbophil inventive gels

| | Wt % Total Polymer | Polycarbophil | 20 RPM TPU1 | 20 RPM Brookfield Viscosity (20 rpm) mPa*s | Yield Value (Stress) Brookfield Pa |
|---|---|---|---|---|---|
| Inventive 11 | 0.5 | 0.25 | 0.25 | 9200 | 61 |
| Inventive 12 | 1 | 0.5 | 0.5 | 72800 | 456 |
| Inventive 13 | 1 | 0.25 | 0.75 | 140,000 | 708 |

As can be seen in the above Table 11, the addition of TPU1 to Polycarbophil exhibits at least one of increased Brookfield viscosity at 20 RPM or yield stress.

TABLE 12

Concentration and Brookfield viscosity data for Ultrez-10 inventive gels

| | Wt % Total Polymer | Ultrez 10 | TPU1 | Brookfield Viscosity (20 rpm) mPa*s | Yield Value (Stress) Brookfield Pa |
|---|---|---|---|---|---|
| Inventive 14 | 0.5 | 0.25 | 0.25 | 42,400 | 220 |
| Inventive 15 | 1 | 0.5 | 1.0 | 101,630 | 988 |
| Inventive 16 | 1 | 0.25 | 0.75 | 133,000 | 1308 |

As can be seen in the above Table 12, the addition of TPU1 to Ultrez 10 increases the Brookfield viscosity at 20 RPM and the yield value increased dramatically.

TABLE 13

Concentration and Brookfield viscosity data ETD 2020 inventive gels

| | Wt % Total Polymer | ETD 2020 | 20 RPM TPU1 | 20 RPM Brookfield Viscosity (20 rpm) mPa*s | Yield Value (Stress) Brookfield Pa |
|---|---|---|---|---|---|
| Inventive 17 | 0.5 | 0.25 | 0.25 | 26,500 | 228 |
| Inventive 18 | 1 | 0.25 | 0.75 | 36,800 | 464 |
| Inventive 19 | 1.5 | 0.5 | 1.0 | 55,000 | 916 |

As can be seen in Table 13, the Inventive examples show similar Brookfield viscosity at 20 rpm due to the higher shear thinning with greater shear and higher Yield value than gels containing the baseline TPU alone.

Lidocaine Drug Loading (Method A)

2 gm Carbopol 980 is dispersed in 190 gm water. 4 gm Lidocaine is dissolved in 8 gm 95% Ethanol. The Lidocaine ethanol is added to the Carbopol dispersion. The TPU solution is added to the Carbopol solution. The pH of the final formulation is 7.02 and the Brook field viscosity 20 rpm is 116,000 mPas. The clarity is 30 nephelometric turbidity units (NTU). This example shows a pharmaceutical gel of high viscosity and high clarity made by the method of blending a Carbomer acid dispersion with pharmaceutical active, lidocaine amine, to partially neutralize the Carbomer, and then blending with the TPU solution.

Lidocaine Drug Loading (Method B)

2 gm Carbopol 980 is dispersed in 190 gm water. 4 gm Lidocaine is dissolved in 8 gm 95% Ethanol. The Lidocaine ethanol is added to the TPU solution. The TPU solution is added to the Carbopol dispersion. The pH of the final formulation is 6.93 and the Brook field viscosity 20 rpm is 115,800 mPas. The clarity is 32 NTU. This example shows a high aqueous content hydroalcoholic gel pharmaceutical gel of high viscosity and high clarity made by the method of dissolving the amine drug lidocaine with the TPU and then blending that with an acid dispersion of Carbomer to obtain a gel of high viscosity and good clarity.

Menthol/Camphor Drug Loaded Hydroalcoholic Example additional Polymer TPU-2

5.4 gm Carbopol 980 is dispersed in 318 gm water. 25 gm menthol and 1.5 gm camphor is dissolved in 37 gm isopropyl alcohol. 30 gm of a 10 wt % solution of TPU-2 (TG-2000) in isopropyl alcohol/water mixtures (80 wt % alcohol) is added to the menthol camphor mixture 0.26 gm triethanol amine is added. The menthol camphor TPU-2 mixture is added to the Carbopol dispersion. (40 wt % alcohol) The pH of the final formulation is and the Brookfield viscosity at 20 rpm is 11,800 mPas. The yield value is 106. The clarity is 30 NTU. This example shows a hydroalcoholic pharmaceutical gel of high viscosity, good yield value, high shear response and high clarity, where menthol and camphor are the active to relieve pain.

Menthol/Camphor Drug Loaded Hydroalcoholic Example additional Polymer TPU-3

1.5 gm Carbopol 980 is dispersed in 156 gm water. 12.5 gm menthol and 0.75 gm camphor is dissolved in 37 gm isopropyl alcohol and 43.3 gm water. 10 gm of a 15 wt % solution of TPU-3 (MPD-371D) in isopropyl alcohol/water mixtures (80 wt % alcohol) is added to the menthol camphor mixture 0.26 gm triethanol amine is added. The menthol camphor TPU-3 mixture is added to the Carbopol dispersion. The Brookfield viscosity at 20 rpm is 26,300 mPas and the formulation is hazy with clarity of 330 NTU. This example shows a 27 wt % isopropanol hydroalcoholic pharmaceutical gel of good viscosity with 0.5 wt % Carbomer and 0.5 wt % TPU-3, where menthol and camphor are the active to relieve pain. The clarity of this gel is adjusted by having a lower alcohol content to give a creamy appearance.

Menthol/Camphor Drug Loaded Hydroalcoholic Example additional Polymer TPU-1

1.5 gm Carbopol 980 is dispersed in 156 gm water. 12.5 gm menthol and 0.75 gm camphor is dissolved in 81 gm isopropyl alcohol and 10 gm water. The menthol camphor mixture is added to the Carbopol dispersion. 100 gm of a 3 wt % solution of TPU-3 (MPD-371D) in water has 0.26 gm triethanol amine added. The TPU-1 mixture is added to the Carbopol menthol camphor dispersion. The Brookfield viscosity at 20 rpm is 65,800 mPas and the formulation is hazy with clarity of 941 NTU. This example shows a 27 wt % isopropanol hydroalcoholic pharmaceutical gel of high viscosity of 0.5 wt % Carbomer and 1 wt % TPU-1, where menthol and camphor are the active to relieve pain. The clarity of this gel has been adjusted by having a lower alcohol content to give a creamy appearance.

Menthol/Camphor Drug Loaded Hydroalcoholic Example Comparison—No TPU 2 gm Carbopol 980 is dispersed in 256 gm water. 16.6 gm menthol and 1 gm camphor is dissolved in 108 gm isopropyl alcohol and 14 gm water. The menthol camphor mixture is added to the Carbopol dispersion and then 0.58 gm triethanol amine is added. The menthol camphor TPU-3 mixture is added to the Carbopol dispersion. The Brookfield viscosity at 20 rpm is 12,250 mPas and the formulation is hazy with clarity of 932 NTU. This example shows a 27 wt % isopropanol hydroalcoholic pharmaceutical gel of 0.5 wt % Carbomer with low viscosity in comparison to the previous examples made with the blend of Carbomer and TPU-3 and TPU-1. Clarity is not influenced by the presence of TPU.

Shear Thinning

Rheology flow curves demonstrate the high viscosity at low shear of the Carbopol and TPU blend, and data calculated from these curves is illustrated in Table 14. Flow curves are generated by measuring shear rate sweeps from 1 to 1000 $s^{-1}$, which gives a measure of thixotropy. Yield stress and microviscosity are estimated from the shear stress and shear rate data by fitting to the Casson rheological model. Yield Stress as determined by the curve Y intercept is another method of demonstrating the high viscosity at no and low shear. Yield Stress may also be determined by Brookfield viscosity measurements at different rpm rates. The yield stress is the applied stress that must be must be exceeded in order to make the gel flow. Higher yield stress will inhibit the flow under the relatively low stresses induced by gravity. For comparison, Mayonnaise is typically about 100 Pa and Hair gel about 135 Pa and Ketchup is 15 Pa.

TABLE 14

Yield stress, Microviscosity and Thixotropic Index of the Baseline and Inventive examples of high viscosity carbomer and the blend of high viscosity Carbomer and TPU1

| Sample # | Wt % Total Polymer | Yield Stress, Pa | Microviscosity, mPa · s | T.I., Pa/s · cm$^3$ |
|---|---|---|---|---|
| Baseline 1A | 0.5 | 66 | 485 | 2030 |
| Baseline 2A | 1 | 114 | 805 | −130 |
| Inventive 1 | 0.25 | 107 | 215 | 5010 |
| Inventive 2 | 0.5 | 235 | 245 | 4790 |
| Inventive 3 | 0.5 | 205 | 990 | 7825 |

TABLE 15

Yield stress, Microviscosity and Thixotropic Index of the Baseline and comparative examples of high viscosity carbomer and the blend of high viscosity Carbomer and PEO PolyOx

| Sample # | Wt % Total Polymer | Yield Stress, Pa | Microviscosity, mPa · s | T.I., Pa/s · cm$^3$ |
|---|---|---|---|---|
| Baseline 1A | 0.5 | 66 | 485 | 2030 |
| Baseline 2A | 1 | 114 | 805 | −130 |
| Comparative 1 | 0.25 | 71 | 55 | 136000 |
| Comparative 2 | 0.5 | 86 | 50 | 113000 |
| Comparative 5 | 1.5 | 88 | 30 | 50500 |

As illustrated in Tables 14 and 15, the inventive samples show higher yield stress than the baseline gels at the same total polymer concentrations (Table 14), as well higher yield stress than the comparative examples at the same blend concentration (Table 14) as measured by the rheometric method. Additionally, the inventive samples show higher microviscosity as measured by the rehometric method than the comparative examples at the same concentration, which is indicative of better spreadability of the hydrogel upon applying shear.

Each of the documents referred to above is incorporated herein by reference, including any prior applications, whether or not specifically listed above, from which priority is claimed. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about." It is to be understood that the upper and lower amount, range, and ratio limits set forth herein may be independently combined. Similarly, the ranges and amounts for each element of the invention can be used together with ranges or amounts for any of the other elements.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of," where "consisting of" excludes any element or step not specified and "consisting essentially of" permits the inclusion of additional un-recited elements or steps that do not materially affect the essential or basic and novel characteristics of the composition or method under consideration.

What is claimed is:

1. A hydrogel blend composition comprising:
    a) a crosslinked polymer derived from one or more olefinically unsaturated polymerizable carboxylic monomers, wherein the crosslinked polymer is partially neutralized;
    b) an optional comonomer; and
    c) a water-soluble thermoplastic polyurethane (TPU) comprising the reaction product of:
        i) a polyisocyanate; and
        ii) a polyol component comprising of at least one polyethylene glycol polyol;
    wherein the composition exhibits high yield stress at low shear.

2. The hydrogel of claim 1, wherein the cross-linked polymer is a carbomer copolymer, a carbomer homopolymer, carbomer interpolymer, or a polycarbophil; and wherein the cross-linked polymer comprises a cross-linking agent is present from about 0.1 to 3.0 weight percent of the cross-linked polymer.

3. The hydrogel of claim 1, wherein the poly(acrylic) acid polymer is cross-linked with an allyl ether cross-linking agent or divinyl glycol.

4. The hydrogel of claim 3, wherein the allyl ether cross-linking agent comprises one or more of allyl pentaerythritol, allyl sucrose, or trimethpropanediolyl ether (TMPDE).

5. The hydrogel of claim 1, wherein the thermoplastic polyurethane comprises the reaction product of (i) at least one aliphatic or aromatic diisocyanate; (ii) a polyol component comprising at one polyethylene glycol polyol having a number average molecular weight of at least 1450 and (ii) optionally, a chain extender component.

6. The hydrogel of claim 5, wherein the aliphatic diisocyanate comprises H12MDI.

7. The hydrogel of claim 5, wherein the aromatic diisocyanate comprises MDI, TDI or XDI.

8. The hydrogel of claim 5, wherein the chain extender comprises an aliphatic diol.

9. The hydrogel of claim 5, wherein the polyol component comprises a blend of polyethylene glycol having number average molecular weights (Mn) of at least 300 and at least 1450.

10. The hydrogel of claim 9, wherein the polyol component comprises a blend of polyethylene glycol having number average molecular weights (Mn) of at least 1450 and at least 8000.

11. The hydrogel of claim 1, further comprising the comonomer, the comonomer comprising one or more of at least one acrylic acid ester of the formula:

wherein $R^3$ is hydrogen, methyl or ethyl and $R^4$ is an alkyl group containing 1 to 30 carbon atoms, in an amount of less than 30 weight percent based upon the weight of the carboxylic acid or anhydride plus the acrylic acid ester.

12. The hydrogel claim 1, wherein the ratio of (a) to (c) is from about 1:9 to about 2:1.

13. The hydrogel of claim 1, wherein the hydrophilic thermoplastic polyurethane forms about 0.01-2.5 wt % of the total weight of the composition.

14. The hydrogel of claim 13, wherein the cross-linked polymer forms from about 0.01 wt % to about 2.5 wt % of the total weight of the composition.

15. The hydrogel of claim 1, further comprising one or more of a pharmaceutical, a biologically active compound, an absorptive material, a personal care compound, an active ingredient, a therapeutic aid, or combinations thereof.

16. A wound covering comprising the hydrogel of claim 1.

17. A gel, a cream or a lotion comprising the hydrogel of claim 1.

18. The hydrogel of claim 1, wherein the thermoplastic polyurethane is a water-soluble TPU.

19. The hydrogel of claim 1, wherein the viscosity of the hydrogel is from 3,000 to 200,000 mPa*s.

20. The hydrogel of claim 1, wherein the hydrogel exhibits a yield stress as measured by Brookfield of from 50 to 2500 Pa.

21. The hydrogel of claim 8, wherein the chain extender component comprises one or more of diethylene glycol or a $C_3$-$C_{12}$ diol and is present in an amount from 0.4 wt % to 4 wt %.

22. A hydrogel blend composition comprising:
    a) a crosslinked polymer derived from one or more olefinically unsaturated polymerizable carboxylic monomers, wherein the crosslinked polymer is partially neutralized;
    b) an optional comonomer; and
    c) a water soluble thermoplastic polyurethane (TPU) comprising the reaction product of:
        i) an aliphatic or aromatic diisocyanate; and
        ii) a polyol component comprising of at least one polyethylene glycol having a number average molecular weight (Mn) of at least 1450;
    wherein the composition exhibits high yield stress at low shear.

23. The hydrogel of claim 22, wherein the aliphatic or aromatic diisocyanate comprises H12MDI, MDI, TDI, or XDI.

24. A process of making a hydrogel composition, said process comprising the steps of: (I) blending:
    a) a crosslinked polymer derived from one or more olefinically unsaturated polymerizable carboxylic monomers, wherein the crosslinked polymer is partially neutralized; and
    b) a water soluble thermoplastic polyurethane comprising the reaction product of:
        i) a polyisocyanate; and
        ii) a polyol component comprising of at least one polyethylene glycol polyol;

wherein the resulting hydrogel composition has a viscosity of from 3,000 to 200,000 mPa*s.

25. A hydrogel blend composition comprising:
a) a homopolymer of a crosslinked polymer derived from one or more olefinically unsaturated polymerizable carboxylic monomers, wherein the crosslinked polymer is partially neutralized; and
b) a hydrophilic thermoplastic polyurethane wherein the hydrogel composition exhibits:
   i) a viscosity of from 3,000 to 200,000 mPa*s; and
   ii) a shear response as measured by microviscosity of from 130 mPa*s to about 2,500 mPa*s.

26. The hydrogel composition of claim 25, wherein the composition exhibits a yield stress as measured by Brookfield of from 50 to 2500 Pa.

* * * * *